US00PP26379P2

(12) United States Plant Patent
Dummen

(10) Patent No.: US PP26,379 P2
(45) Date of Patent: Feb. 2, 2016

(54) ***VERBENA* PLANT NAMED 'DUEMPFLAPUS'**

(50) Latin Name: *Verbena hybrida*
Varietal Denomination: Duempflapus

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 3 days.

(21) Appl. No.: 14/120,880

(22) Filed: Jul. 7, 2014

(51) Int. Cl.
*A01H 5/02* (2006.01)

(52) U.S. Cl.
USPC ..... Plt./308

(58) Field of Classification Search
USPC ..... Plt./308
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Verbena* plant named 'Duempflapus', characterized by its compact, semi-upright and mounding plant habit; vigorous growth habit; freely branching habit; freely flowering habit; and large purple-colored flowers.

1 Drawing Sheet

Botanical designation: *Verbena hybrida.*
Cultivar denomination: 'DUEMPFLAPUS'.

BACKGROUND OF THE INVENTION

The present invention relates to a new and distinct cultivar of *Verbena* plant, botanically known as *Verbena hybrida* and hereinafter referred to by the name 'Duempflapus'.

The new *Verbena* plant is a product of a planned breeding program conducted by the Inventor in Rheinberg, Germany. The objective of the breeding program is to create new compact and semi-upright *Verbena* plants with numerous large and attractive flowers.

The new *Verbena* plant originated from a cross-pollination made by the Inventor in July, 2011 in Rheinberg, Germany of a proprietary selection of *Verbena hybrida* identified as code number V10-1499-002, not patented, as the female, or seed, parent with a proprietary selection of *Verbena hybrida* identified as code number F-22-1209, not patented, as the male, or pollen, parent. The new *Verbena* plant was discovered and selected by the Inventor as a single flowering plant within the progeny of the stated cross-pollination in a controlled greenhouse environment in Rheinberg, Germany in May, 2013.

Asexual reproduction of the new *Verbena* plant by terminal cuttings in a controlled greenhouse environment in Rheinberg, Germany since June, 2013 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duempflapus'. These characteristics in combination distinguish 'Duempflapus' as a new and distinct *Verbena* plant:

1. Compact, semi-upright and mounding plant habit.
2. Vigorous growth habit.
3. Freely branching habit.
4. Freely flowering habit.
5. Large purple-colored flowers; flowers held above and beyond the foliar plane in mounded umbels.

Plants of the new *Verbena* differ from plants of the female parent selection primarily in flower color as plants of the female parent selection have red-colored flowers. In addition, plants of the new *Verbena* are more compact than plants of the female parent selection.

Plants of the new *Verbena* differ from plants of the male parent selection primarily in flower color as plants of the male parent selection have light lavender-colored flowers. In addition, plants of the new *Verbena* are not as compact as plants of the male parent selection.

Plants of the new *Verbena* can be compared to plants of the *Verbena hybrida* 'Lan Bule', disclosed in U.S. Plant Pat. No. 15,604. In side-by-side comparisons conducted in Rheinberg, Germany, plants of the new *Verbena* differed from plants of 'Lan Bule' in the following characteristics:

1. Plants of the new *Verbena* were more freely branching than plants of 'Lan Bule'.
2. Plants of the new *Verbena* had larger leaves than plants of 'Lan Bule'.
3. Plants of the new *Verbena* were more freely flowering than plants of 'Lan Bule'.
4. Plants of the new *Verbena* had larger flowers than plants of 'Lan Bule'.
5. Plants of the new *Verbena* and 'Lan Bule' differed in flower color as plants of 'Lan Bule' had dark blue violet-colored flowers.
6. Plants of the new *Verbena* had shorter peduncles than plants of 'Lan Bule'.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant.

The photograph is a side perspective view of a typical flowering plant of 'Duempflapus'.

DETAILED BOTANICAL DESCRIPTION

The aforementioned photograph and following observations, measurements and values describe plants grown in 12-cm containers during the summer in a glass-covered greenhouse in Rheinberg, Germany and under cultural practices typical of commercial *Verbena* production. During the production of the plants, day and night temperatures averaged 18° C. and light levels averaged 4,500 lux. Plants were pinched one time three weeks after planting and were ten weeks old when the photograph and the description were taken. In the description, color references are made to The Royal Horticultural Society Colour Chart, 2007 Edition, except where general terms of ordinary dictionary significance are used.

Botanical classification: *Verbena hybrida* 'Duempflapus'.

Parentage:

*Female, or seed, parent*.—Proprietary selection of *Verbena hybrida* identified as code number V10-1409-002, not patented.

*Male, or pollen, parent*.—Proprietary selection of *Verbena hybrida* identified as code number F-22-1209, not patented.

Propagation:

*Type*.—Terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; white in color.

*Rooting habit*.—Freely branching; dense.

Plant description:

*Plant habit*.—Compact, semi-upright and mounding plant habit; freely branching habit with about eight to nine primary lateral branches with secondary lateral branches potentially forming at every node; pinching enhances lateral branch development; dense and bushy plant habit; vigorous growth habit.

*Plant height*.—About 25.5 cm.

*Plant diameter*.—About 64 cm.

Lateral branch description:

*Length*.—About 20 cm.

*Diameter*.—About 3 mm.

*Internode length*.—About 2.5 cm.

*Texture*.—Pubescent.

*Strength*.—Strong.

*Color*.—Close to 144A.

Leaf description:

*Arrangement*.—Opposite, simple.

*Length*.—About 4.1 cm.

*Width*.—About 1.6 cm.

*Shape*.—Lanceolate.

*Apex*.—Acute.

*Base*.—Attenuate.

*Margin*.—Lobed.

*Texture, upper and lower surfaces*.—Pubescent, coarse.

*Venation pattern*.—Pinnate.

*Color*.—Developing leaves, upper surface: Close to 137A. Developing leaves, lower surface: Close to 137D. Fully expanded leaves, upper surface: Close to 137C; venation, close to 137C. Fully expanded leaves, lower surface: Close to 138B; venation, close to 139D.

*Petioles*.—Length: About 4.2 mm. Diameter: About 1.6 mm. Texture, upper and lower surfaces: Smooth, glabrous. Color, upper and lower surfaces: Close to 138D.

Flower description:

*Flower arrangement and habit*.—Salverform flowers arranged in hemispherical terminal umbels; umbels dense and mounding; numerous umbels per plant; flowers face upward or outwardly depending on position in the umbel; freely flowering habit with about 15 to 18 flowers per inflorescence and about 450 to 570 flowers developing per plant.

*Fragrance*.—None detected.

*Natural flowering season*.—Plants flower continuously from the spring through the fall in Germany; plants begin flowering about eight weeks after planting.

*Flower longevity*.—Individual flowers last about one week on the plant; flowers persistent.

*Inflorescence height*.—About 3.4 cm.

*Inflorescence diameter*.—About 4.75 cm.

*Flower buds*.—Length: About 1.5 cm. Diameter: About 1.6 mm. Shape: Oval to tubular. Color: Close to 86A.

*Flowers*.—Appearance: Salverform, five-parted fused corolla. Diameter: About 2.1 cm. Depth: About 3.2 cm. Throat diameter: About 2.4 mm. Tube length: About 2.2 cm.

*Corolla*.—Arrangement: Single whorl of five fused petals. Petal lobe length: About 9.2 mm. Petal lobe width: About 8.2 mm. Petal lobe shape: Obovate. Petal lobe apex: Emarginate. Petal margin: Entire. Petal texture, upper and lower surfaces: Smooth, glabrous. Throat texture: Smooth, glabrous. Tube texture: Smooth, glabrous. Color: Petal lobe, when opening, upper surface: Close to 78A. Petal lobe, when opening, lower surface: Close to 78C. Petal lobe, fully opened, upper surface: Close to 78B; color becoming closer to 88B with development. Petal lobe, fully opened, lower surface: Close to 78D. Throat: Close to 157C. Tube: Close to 157C.

*Calyx*.—Arrangement: Star-shaped calyx with five fused sepals. Sepal length: About 1.3 cm. Sepal width: About 2 mm. Sepal shape: Ligulate. Sepal apex: Acute. Sepal margin: Entire. Sepal texture, upper and lower surfaces: Pubescent, coarse. Sepal color, upper and lower surfaces: Close to 143A.

*Peduncles*.—Length: About 2.75 cm. Diameter: About 2 mm. Strength: Strong. Texture: Pubescent. Color: Close to 144B.

*Pedicels*.—Length: About 0.5 mm. Diameter: About 0.5 mm. Strength: Strong. Texture: Smooth, glabrous. Color: Close to 144A.

*Reproductive organs*.—Stamens: Quantity and arrangement: About four per flower, adnate to corolla tube. Anther length: About 1 mm. Anther shape: Oval. Anther color: Close to 149A. Pollen amount: Moderate. Pollen color: Close to 2D. Pistils: Quantity: One per flower. Pistil length: About 1.9 cm. Stigma shape: Bi-parted. Stigma color: Close to 140B. Style length: About 1.8 cm. Style color: Close to 157B. Ovary color: Close to 143B. Fruits and seeds: Fruit and seed development has not been observed on plants of the new *Verbena*.

Temperature tolerance: Plants of the new *Verbena* have been observed to tolerate temperatures from about 5° C. to about 40° C.

Pathogen & pest resistance: Plants of the new *Verbena* have not been observed to be resistant to pathogens and pests common to *Verbena* plants.

It is claimed:

1. A new and distinct *Verbena* plant named 'Duempflapus' as illustrated and described.

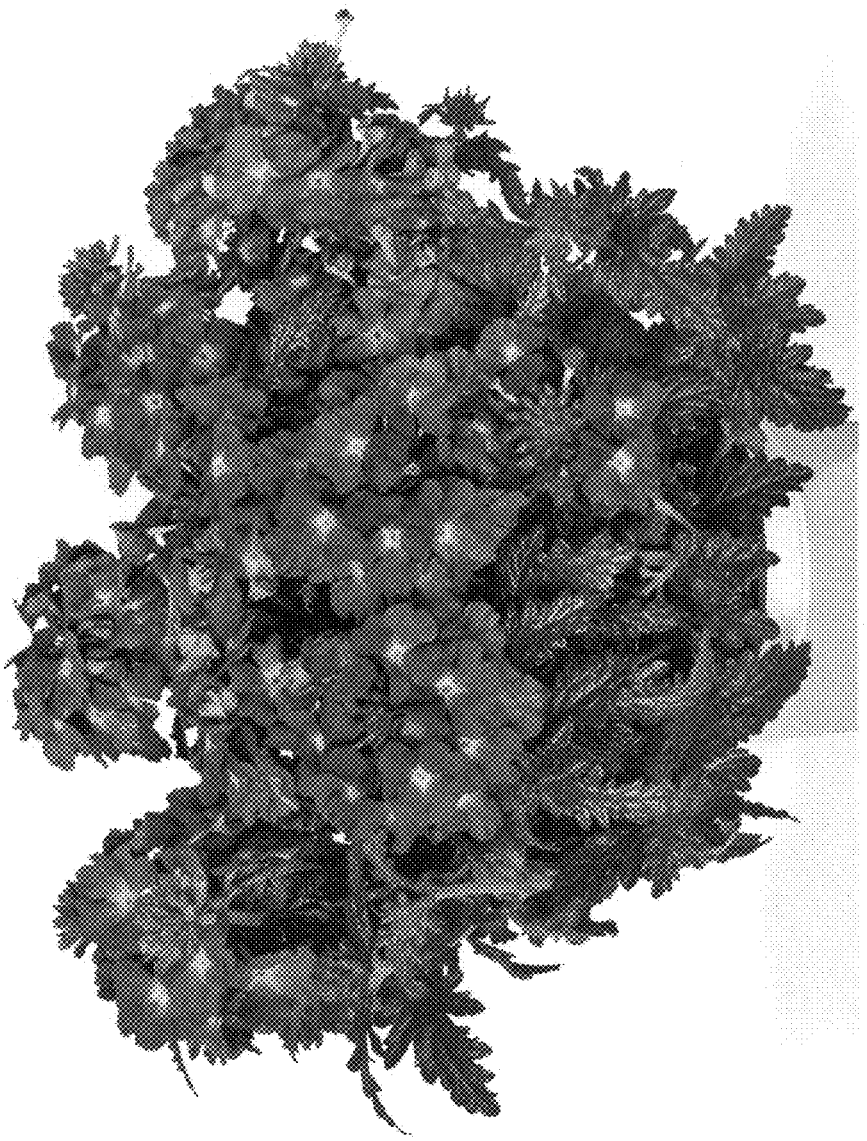

* * * * *